United States Patent
Lefkovitz

(10) Patent No.: US 10,493,264 B1
(45) Date of Patent: Dec. 3, 2019

(54) TRANSCUTANEOUS ELECTRICAL NERVE STIMULATOR

(71) Applicant: Joshua A. Lefkovitz, Wasworth, OH (US)

(72) Inventor: Joshua A. Lefkovitz, Wasworth, OH (US)

(*) Notice: Subject to any disclaimer, the term of this patent is extended or adjusted under 35 U.S.C. 154(b) by 0 days.

(21) Appl. No.: 15/425,994

(22) Filed: Feb. 6, 2017

Related U.S. Application Data

(60) Provisional application No. 62/426,244, filed on Nov. 24, 2016, provisional application No. 62/290,989, filed on Feb. 4, 2016.

(51) Int. Cl.
| | | |
|---|---|---|
| *A61B 5/00* | (2006.01) | |
| *A61N 1/04* | (2006.01) | |
| *A61N 1/36* | (2006.01) | |

(52) U.S. Cl.
CPC .......... *A61N 1/0456* (2013.01); *A61B 5/4824* (2013.01); *A61N 1/0492* (2013.01); *A61N 1/36021* (2013.01)

(58) Field of Classification Search
CPC ................ A61N 1/0456; A61N 1/0492; A61N 1/36021; A61B 5/4824
See application file for complete search history.

(56) References Cited

U.S. PATENT DOCUMENTS

| | | | | |
|---|---|---|---|---|
| 6,445,955 | B1* | 9/2002 | Michelson | A61N 1/36003 607/2 |
| 2007/0088419 | A1* | 4/2007 | Fiorina | A61N 1/0476 607/152 |
| 2008/0288035 | A1* | 11/2008 | Gill | A61F 7/007 607/108 |

* cited by examiner

*Primary Examiner* — George Manuel
(74) *Attorney, Agent, or Firm* — Sand, Sebolt & Wernow Co., LPA

(57) ABSTRACT

A TENS system is provided having an electrode element design accommodating improved motion mechanics and maneuverability while maintaining electrical contact. An electrode having a soft wing construction is provided such that a multi-planar flexibility is provided during operation. A range of motion hinge provides and positions at a central area of a winged configuration a housing such that both a rotational movement and an angular movement may occur while maintaining continuous, direct contact with the TENS electronics within the housing. A selected die-cut pattern of a number of designs may form a stepped-in wing configuration may further contribute to a lateral flexibility of the wings.

17 Claims, 5 Drawing Sheets

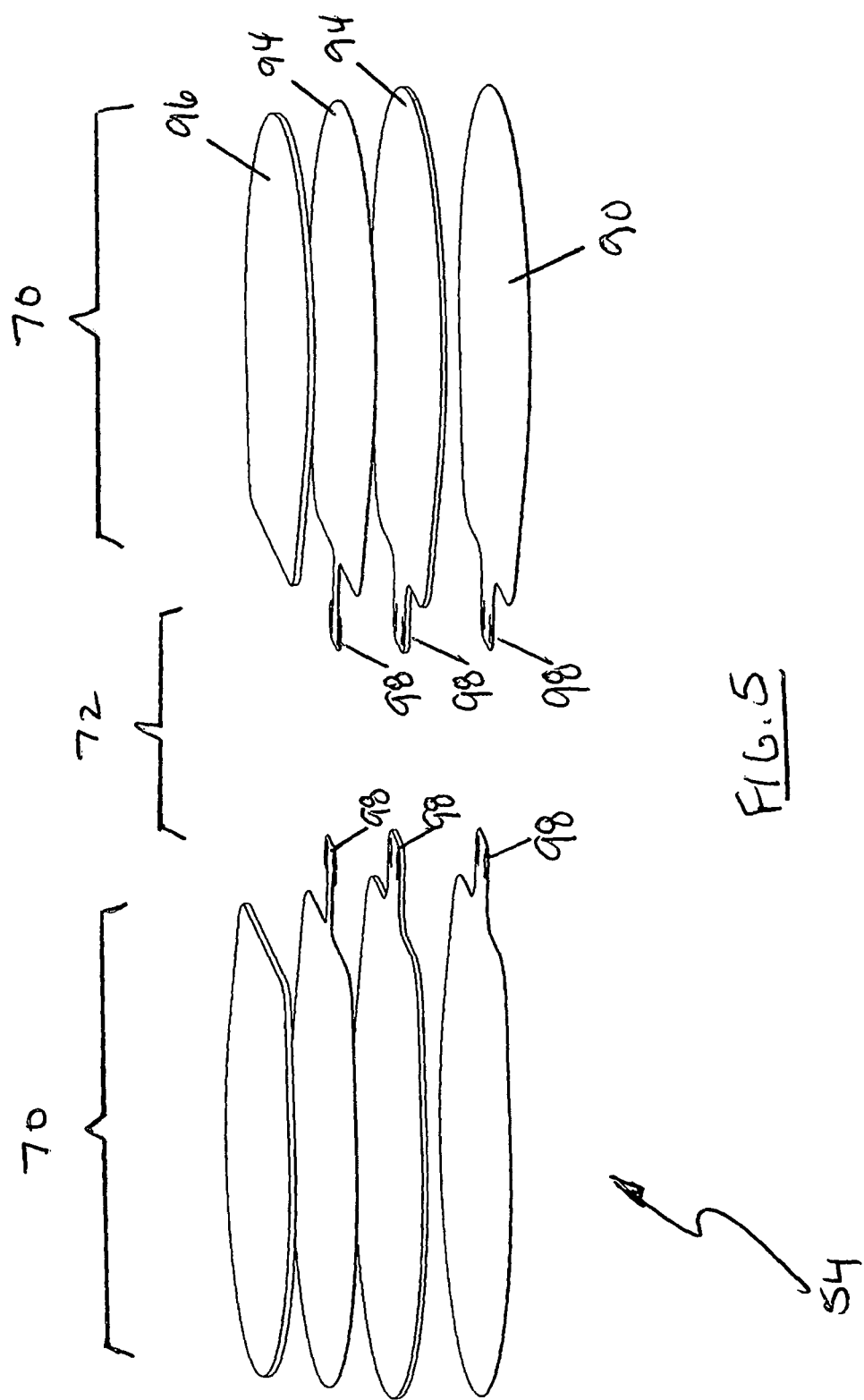

TRANSCUTANEOUS ELECTRICAL NERVE STIMULATOR

RELATED APPLICATIONS

The present invention claims the benefit of U.S. Provisional Application 62/290,989 filed on Feb. 4, 2016 and U.S. Provisional Application 62/426,244 filed on Nov. 24, 2016, both incorporated by reference as if fully rewritten herein.

BACKGROUND OF THE INVENTION

1. Field of the Invention

The present invention relates to transcutaneous electrical nerve stimulation ("TENS") systems and, more particularly, to an improved TENS system that incorporates functional anatomical shaped electrodes that enables bio-movement.

2. Description of the Related Art

In the treatment of chronic pain, the identification of the pain causation, and the appropriate application of a therapeutic to cause a beneficial effect without adverse side effects has long been a troublesome area of medical practice. "Chronic pain" is a diagnosis that is less a true diagnosis of the physiological condition than a symptomatic diagnosis describing a chronic condition.

One treatment for such chronic pain is through the use of a Transcutaneous Electrical Nerve Stimulator (TENS) device. The TENS unit is a dual channel device that typically delivers 0.5 to 200 pulses per second at a pulse width of between about 50 and 250 microseconds. The patient receives 2 to 4 electrodes around the area of pain for as long as needed. The amplitude of the TENS wave is adjusted until the patient feels sensory input that is pleasurable and not uncomfortable. If the TENS treatment benefits the patient, the physician/therapist often recommends that a TENS unit be rented and/or purchased for the patient for home use, particularly for sessions in between interferential treatments.

An exemplary TENS device that is currently commercially available may use a battery, such as a 9 volt battery which is sufficient because of the relative low output required for the use of this device. The TENS unit typically a portable device that the patient can wear and use on a 24 hour basis without the constraint of a lack of electrical energy due to insufficient battery capabilities.

This ability for a patient to be able to wear such a portable device on an ongoing basis results in the identification of some problems or limitations. Attachment of electrodes to an anatomical surface over a long period of time creates limitations on both comfort and connection. The lack of flexibility of conventional electrode patches provide resistance to movement that can increase irritation or decrease conductivity. This can be especially at issue when used at high movement anatomical surfaces such as joints.

It is thus an object of the present invention to provide an improved TENS system.

It is one feature of the present invention to provide an improved TENS system that incorporates functional anatomical shaped multilayer electrodes that enable bio-movement.

It is another feature of the present invention to provide such improved electrodes that incorporate a laser printed conductive silver paint as a conductive surface.

It is yet another feature of the present invention to provide such improved electrodes that form a flexible winged configuration.

It is yet another feature of the present invention to provide a system for electrical pathway or channel cleaning. Such an improvement will allow for maintaining circuit operation and prevention of degradation in current over time.

It is still yet another feature of the present invention to provide a TENS system that can be controlled through operation of a smart device application. Such operation may further accommodate remote monitoring, manipulation or control. Further, the improved TENS system is provided that utilizes a mobile application software that enables treatment regimes broken down into body parts or conditions, and that further incorporates a pain tracking feature that measures pain before and after a treatment such as to allow a pain reduction differential to be tracked, charted and graphed. The use of pain scale tracking and charting allows for user feedback to identify efficacy of treatment modalities.

According to one aspect of the present invention, an improved TENS system is provided having an electrode element design accommodating improved motion mechanics and maneuverability while maintaining electrical contact. In such an aspect an electrode having a soft wing construction is provided such that a multi-planar flexibility is provided during operation. Within a design consistent with such an aspect of the invention a range of motion hinge may be provided and positioned at a central area of a winged configuration such that both a rotational movement and an angular movement may occur. A selected die-cut pattern of a number of designs may form a stepped-in wing configuration may further contribute to a lateral flexibility of the wings.

Alternate configurations may provide multi-planar flexibility in a variety of ways, including, inter alia, a hinge mechanism or a ball-joint connection between the device body and the electrode wings in order to achieve such features and advantages.

According to another aspect of the present invention, such electrodes may be formed of medical grade silver paste with additives for enhancing conductivity and durability. Such multi-layered silver composite is supported onto a lower exterior surface of an electrode wing membrane substrate.

According to another aspect of the present invention, an improved TENS system is provided in which the improved depolarization of conductive current is provided to counteract the adverse effects associated with typical adhesive gels. Such adhesive gel contain impurities such as sulfur. Sulfur and other ions inside such gel will naturally move from cathode to anode through an electrokinetic effect. Where the anode and cathode are made using a silver substrate, an unbalanced electrical field can form with more charge accumulation near the anode than cathode (or vice versa). When ions accumulate in one pole of the electrode, accumulated ions can build and react with silver (e.g. in the case of sulfur ions, a reaction results in silver sulfide). Such chemical reactions create dirt and corrosion on the surface of the silver substrate which is both unsightly and can adversely affect impedence of the electrodes. In such an aspect of the present invention, balancing of the electrical field is provided by sensing and measuring the varied balance of accumulated ions, and shifting the polarity such that the un-even accumulation of the ions is dispersed and equalized. Management of such rebalancing may be programmed in the control firmware to continuously maintain this task.

According to yet another aspect of the present invention, an improved TENS system is provided that utilizes a mobile application software that enables treatment regimes broken down into body parts or conditions, and that further incorporates a pain tracking feature that measures pain before and after a treatment such as to allow a pain reduction differential to be tracked, charted and graphed. The use of pain scale tracking and charting allows for user feedback to identify efficacy of treatment modalities. Tracking and charting features may be used to provide efficacy feedback such that the user may correlate pain reduction results of each tracked program, and thus then draw conclusions as to which program is best. Additionally, remote operation and reset as well as auto-reconnect features may be utilized for remotely controlled or automatically controlled operation.

Further objects, features, benefits and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 5 is an exploded perspective view of an electrodes 54 according to a preferred arrangement

DESCRIPTION OF THE PREFERRED EMBODIMENTS

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

The best mode for carrying out the invention is presented in terms of its preferred embodiment, herein depicted within the Figures.

1. Detailed Description of the Figures

Figure 1:
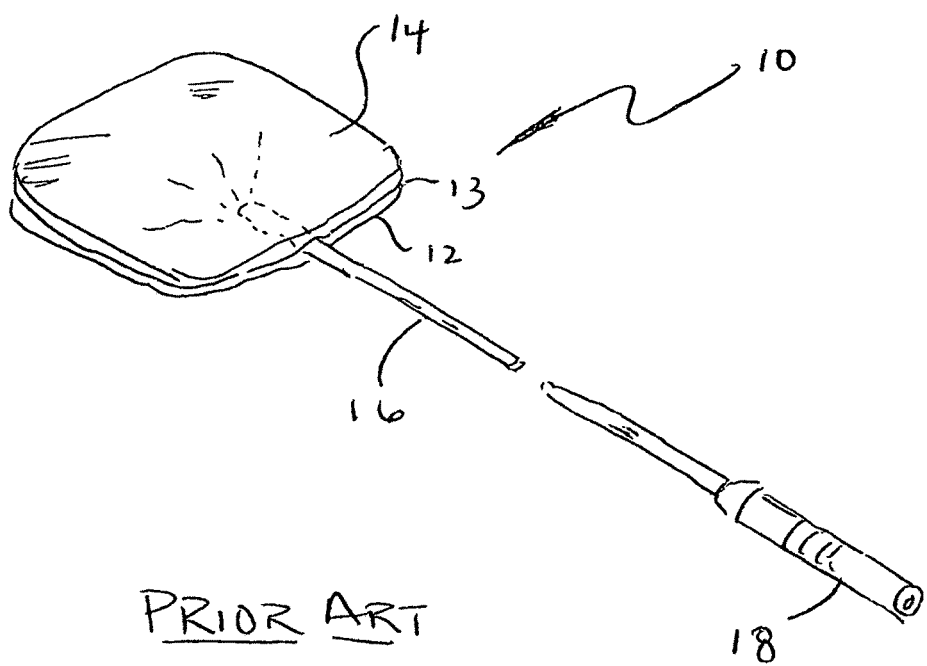
FIG. 1 depicts a conventional TENS electrode according to the PRIOR ART.
Figure 2:
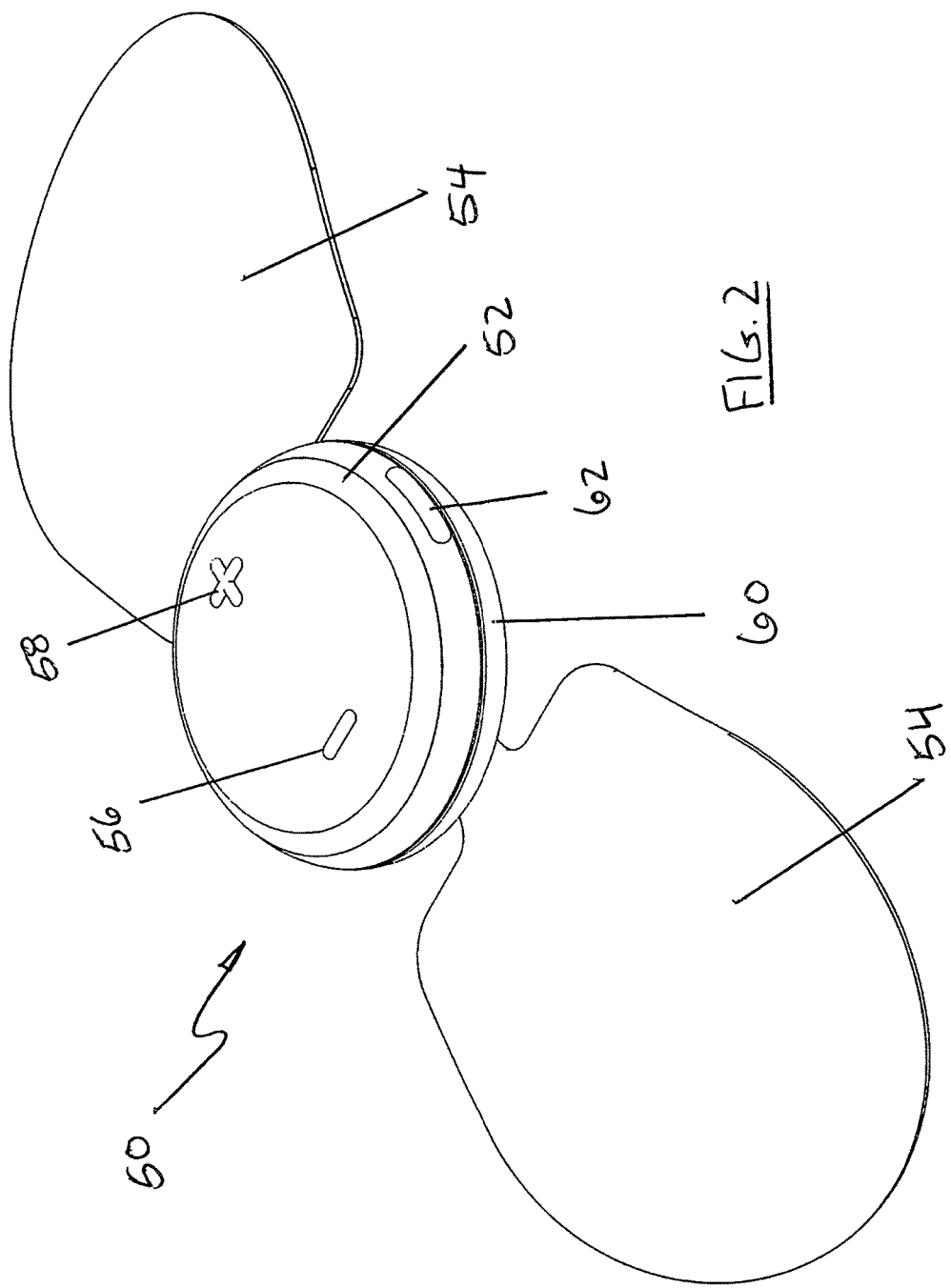
FIG. 2 is a top perspective view of an improved TENS system according to the preferred embodiment of the present invention that incorporates functional anatomical shaped electrodes that enables bio-movement.

Referring to FIG. 1, the structure of a conventional TENS electrode 10 is shown according to the PRIOR ART. Such an electrode 10 comprises a layer of self-adhesive conductive gel 12, a conductive body 13 mounted on the self-adhesive conductive gel 12, an isolating tape 14 mounted on the conductive body 13. A lead wire 16 with the first terminal electrically provided between the conductive body 13 and the isolating tape 14. The self-adhesive conductive gel 12 is made of electrically conductive material to direct electrical current into the body. The self-adhesive conductive gel 12 is to be positioned at the treatment site on the skin. The second terminal 18 of the lead wire 16 connects the TENS.

Conventionally, the material to fabricate the conductive body 13 is chosen from aluminum foil, stainless steel fiber or carbon film. When made of aluminum foil, low conductivity will be expected.

While utilizing a conductive body 13 of stainless steel/polyester fiber, flexibility and surface conformance may be increased, but such materials are vulnerable to electromagnetic interference from nearby electrical appliance and further have decreased impedances that can be as low as 10-20 ohms per square inch. When the conductive body 13 is made of another nonmetal material, such as carbon film, electromagnetic interference caused by nearby electrical appliance can be avoided. However, the carbon film has a moderate level of conductivity.

Referring now in conjunction with FIG. 2 through FIG. 5, wherein like reference numerals indicate the same parts throughout the several views, an improved TENS system, generally noted as 50, is provided according to the preferred embodiment of the present invention. The TENS unit 50 consists of a portable, disc shaped housing 52 in electrical communication with a functional anatomical shaped electrode 54 that enables bio-movement.

In this particular embodiment the case or housing 52 is equipped with an attachment mechanism (not shown) that affixes directly to the electrode 54 such that when the electrode 54 is attached to a user (as described in greater detail below) the housing 52 is supported directly thereon during use. In such a configuration, the electrode 54 provides both electrical communication to the user's skin surface, as well as a housing support. Further, the electrode 54 is intended as having a design that accommodates a wider range of motion mechanics, improved user maneuverability, and increased maintenance of electrical contact. As shown herein the electrode is configured having a soft wing construction is provided such that a multi-planar flexibility. Such preferred embodiment will be described in greater detail below. However, it should be noted and understood that such a desig n in intended to provide just one form factor that enables the present invention and, as such, is not intended to be comprehensive of all intended designs. Rather, a person having ordinary skill in the relevant art, in light of the present teachings, should understand that various other designs may exist consistent with the invention. Consequently, it is intended that within the range of equivalents the present invention should be considered broadly as including those features and elements that provide the equivalent or similar functionality as a range of motion hinge provided and positioned at a central area of a winged configuration such that both a rotational movement and an angular movement may occur. Alternate configurations may provide multi-planar flexibility in a variety of ways, including, inter alis, a hinge mechanism or a ball-joint connection between the device body and the electrode wings in order to achieve such features and advantages. Consistent with this broad range of equivalence, an exemplary alternate configuration is shown above in conjunction with FIG. 6a-6b and described therewith in greater detail below.

The outer surface if the case 52 may further be equipped with a selector switch 56 or other equivalent mechanism to be used to set the beat frequency (i.e., the modulating frequency for turning the carrier signal on and off at a predetermined frequency characteristic of the therapeutic treatment being performed). In this particular illustrated embodiment only two frequency settings are available to the user (typically 9.125 Hz or 292 Hz). As such this particular embodiment is easily operated by the patient.

In a more complex embodiment, it is envisioned and should therefor be understood by one having ordinary skill in the relevant art in light of the current teachings that a greater number of preselected discrete frequency settings may be provided by, for example, making the slot 58 of the sliding selector switch 56 longer. It should be apparent, by a person having ordinary skill in the relevant art in light of the present teachings, that this and other such variations should be considered as either mere design choices or otherwise within the range of equivalents of the present invention. Other such variations may include a side face 60 of the case 52 may further be provided with an on/off switch 62 and/or a monitor light 64 along with an electrical current selector switch 56.

Figure 3:
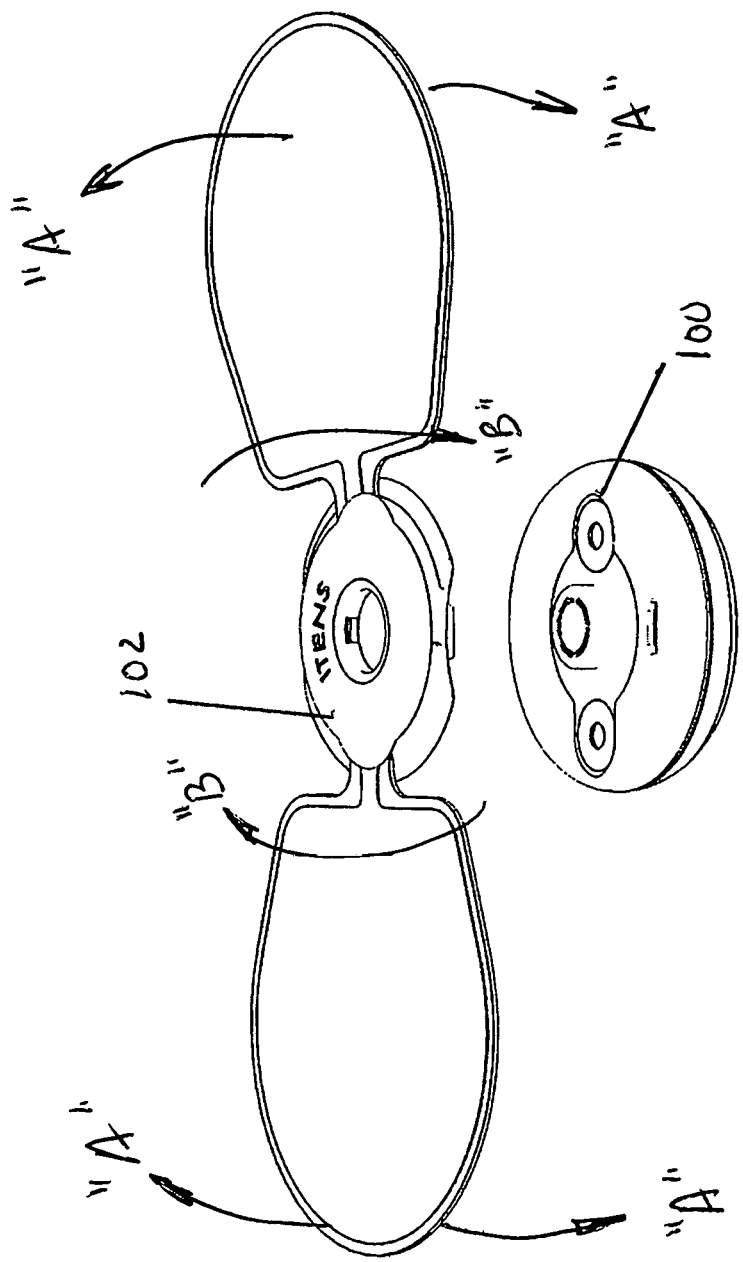
FIG. 3 is a bottom perspective view thereof shown with the electrode 54 removed from the housing 52.

Referring in greater detail in conjunction with FIG. 3 and FIG. 5, a construction of the electrode 54 and its connection to the housing 52 is shown. The electrode 54 may be formed as a die cut body that incorporates a functional anatomical shaped that enables bio-movement. Such a preferred functional anatomical shape may include a biconic, butterfly, hourglass or dogbone shaped planar member of various sizes having a pair of planar, opposed wing membranes 70 extending bilaterally from a central housing attachment zone 72 (as described in greater detail below). It is intended that various sized and shaped electrodes that may be provided adapted for use in conjunction with any of a number of specific high movement anatomical attachment points. These may include such joints as the ankle, knee, elbow, or wrist. Further, other more general moderate movement anatomical attachment points may be further accommodated through various sized planar electrodes 54 that provide rotation of the opposing wind membranes 70 about the attachment zone 72 about multiple planes or directions, including a first direction "A" in an up/down motion and a second direction "B" in a torsional, twisting motion. Also intended are attachment zones 72 of small sizes for small treatment areas through larger sized for large treatment areas.

As shown, an individual electrode 54 may be constructed in a multi-layer structure. An outer layer 90 is formed of a thermoplastic polyurethane ("TPU") membrane or similar material having properties including elasticity, transparency, and resistance to oil, grease and abrasion. The outer layer 90 is die cut with a stepped-in 98 wing configuration provide mechanical/physical protection of the overall electrode assembly. Motion mechanics/maneuverability with a soft wing construction is thereby provided with a multi-planar flexibility to provide a range of motion hinge in the central area 72 of the winged configuration such that a rotational movement "B" can occur while also providing lateral flexibility "A" of the wings 70. A first inner layer 92 is formed of polyethylene terephthalate("PET") and forms a water or moisture barrier. Next is a second inner conductive layer 94. In a preferred embodiment, the conductive layer 94 us formed by laser printing a conductive silver paint onto the first inner layer 92. It has been found that the use of a conductive metal based paint for use with the electrode surface allows for improved flexibility of the electrode about an anatomical surface (as compared to conventional electrode patches) and provide less resistance to movement, while still providing an surface having increased conductivity. Finally, an adhesive inner surface 96 is provided as a final layer of an adhesive gel to be peel-n-stick and self-applied and self-removed for a continuous reuse.

Typical adhesive gel contains impurities, such as sulfur, that can create a silver sulfide impurity on the silver substrate as an electrical field is passed between cathode to anode. When such ionic impurities accumulate in one pole of the electrode through electrophoretic action, an unbalancing in the electrical field and/or increased impedance/resistence can result. The use of medical grade silver paste enhanced with a conductivity and durability additive and added in a multi-layered format onto the lower exterior surface of the wing, in combination with electrical resistance compensation (as described in greater detail below) shift the polarity such that the un-even accumulation of the ions is dispersed and equalized.

The various layers 90-96 are assembled in a laminate fashion to form the pair of electrode attachment surfaces 70 laterally extended about the central housing attachment hub 72 that is formed to allow for the electrodes to be interconnected to the TENS unit 52 by way of a firm magnetic connection. As shown best in conjunction with FIG. 4, the electrode 54 may be affixed between a base plate 100 and a hub or locking ring 102. Such a direct connection may be magnetically maintained or accomplished by mechanical impingement or mechanical attachment. Such a configuration allows further for the elimination of lead wires between the operational electronics within the housing 52 and the electrode conductive surface elements 70. The base plate 100 may similarly attach to the housing 52, which may be formed as an assembly of a lower housing element 52a and an upper housing element 52b that may contain a contact/connection magnet 104, a power source 106, and a circuit board 108. The incorporation of a micro USB connection 110 or similar physical communication connection, or a wireless communication mechanism 112 such as a Bluetooth® communication module 114 can alternately provide operational control, data output or other input/output with the electronics.

Figure 4:
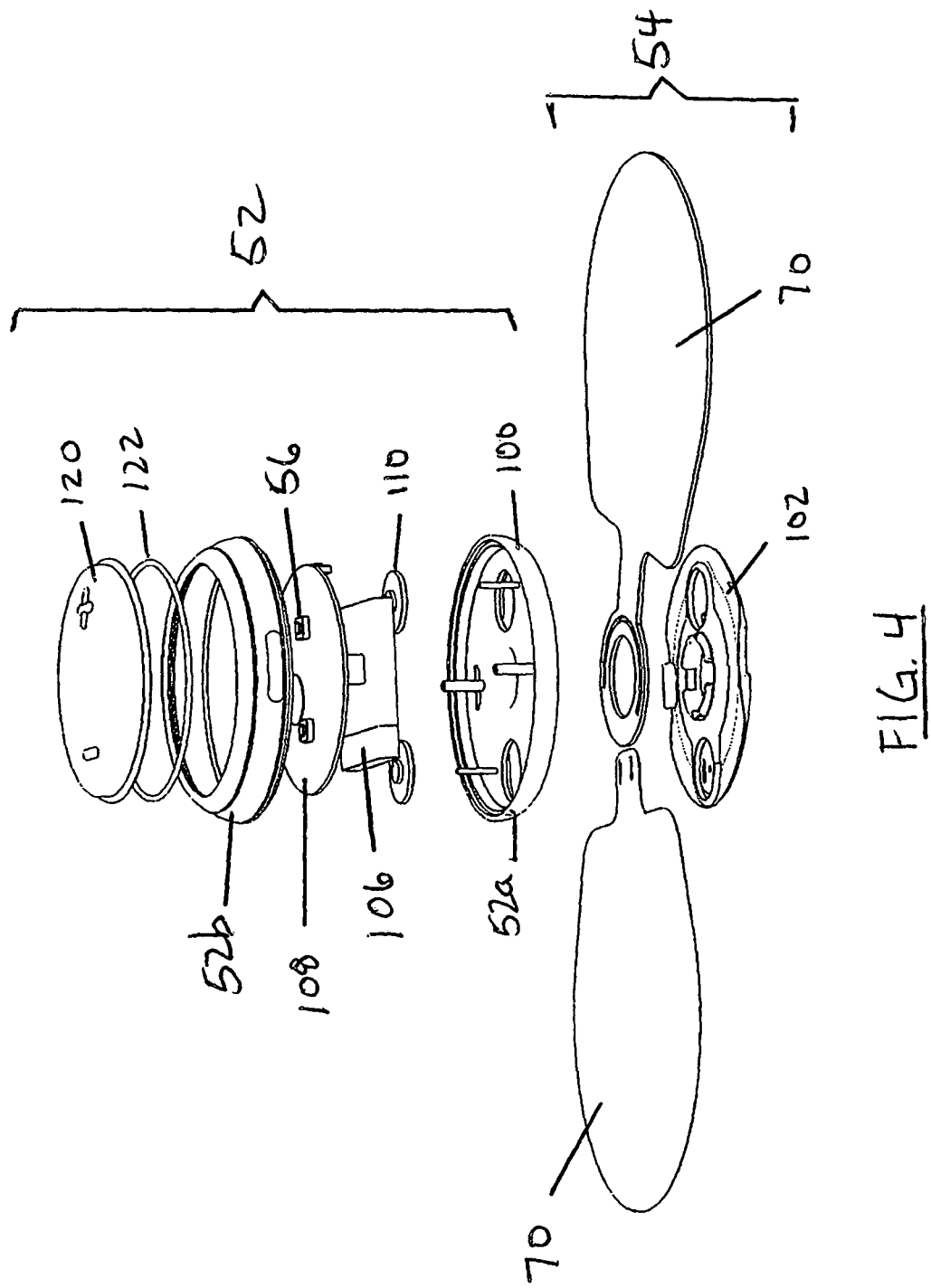
FIG. 4 is a top exploded perspective view thereof.

While various control schemes may be utilized for operation, one such design choice shown in conjunction with FIG. 4 includes the use of a separate on/off switch 56 and intensity control. As shown in one implementation, the intensity control may include a rotatable dial 120 held in place in the upper hosing 52b. A sealing mechanism 122 may further maintain the physical integrity of such a rotatable intensity control.

As should be now understood by a person having ordinary skill in the relevant art in light of the above teachings, it should be understood that variations within the actual implementation may be provide while still staying within the scope, substance, function and intent of the present invention. By way of example, and not meant as a limitation, variations in the patterns and structure of the electrodes, variations in the geometry of the electrode-housing form factor, and variations in the implementation of the maneuverability and motion mechanics of the electrodes may all be subject to modification. Such modification should be considered within the broad range of equivalents of the present disclosure.

Variations in the patterns and structure of the electrodes are envisioned.

Variations in the geometry of the electrode-housing form factor are also envisioned. By way of example, and not as a limitation, a round planar electrode may be formed angularly about a disc shaped housing 52. Such a design may provide a substantial benefits described by the present invention in a most compact overall form factor.

Variations in the implementation of the maneuverability and motion mechanics of the electrodes may all be subject to modification. An alternate functional anatomical shape may be provided that enables bio-movement through laterally swinging attachment of the electrodes about a central housing 54 hub.

Other features, otherwise convention by themselves, may be included in conjunction with the present invention. One example may include the TENS unit 50 being supplied in a kit having multiple different and multiple different sized electrodes, such a multiple electrodes made available in a multiple colors, patterns, sizes or configurations. Further anticipated is the TENS system 50 being used in conjunction with operational accessories, such as a charger and charging cord that may be used in conjunction with a rechargeable battery source for operating the TENS unit 50.

2. Operation of the Preferred Embodiment

In operation, the actual use of the TENS unit 50 is relatively simple and straightforward. The electrodes 54, typically as a pair of self adhering neurostimulation electrodes, are positioned on mammalian skin tissue in accordance with a health care professional or physician's instructions. The frequency selector 562 can be positioned either high, e.g. 292 Hz, or low, e.g. 9.125 Hz. The on/off switch 62 when turned on will activate the on light 64 which flashes or blinks faster as the current setting is increased. As such, visual confirmation of the instrument being on and the particular current setting can be readily determined by looking at the light 64. During use the current can be adjusted by the user by use of switch 56. Typically the current is initially elevated until the perception of electrical stimulation is perceived. The current is then decreased until perception of stimulation is undetectable. Readjustment during treatment can be repeated as needed.

Finally, it is a further element of the present invention to provide such a described improved TENS system 50 that utilizes a mobile application software that is generally shown in conjunction with FIG. 10, that enables treatment regimes broken down into body parts or conditions, and that further incorporates a pain tracking feature that measures pain before and after a treatment such as to allow a pain reduction differential to be tracked, charted and graphed. The use of pain scale tracking and charting allows for user feedback to identify efficacy of treatment modalities. Additional tracking and charting functionality may also be provided through a smart device application. Such a software interface can provide access to feature such that the program treatment modes that may be tracked and charted such that the user can see the pain reduction results of each tracked program, and thus then draw conclusions as to which program is best. Further provided may include electrical pathway channeling to provide a conductive channeling of currents for creating unique and non-traditional configurations for electrode sizes such that the current is directed in a defined orientation such as to establish an anode and cathode separation.

The foregoing descriptions of specific embodiments of the present invention are presented for purposes of illustration and description. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of *Warner-Jenkinson Company*, v. *Hilton Davis Chemical*, 520 US 17 (1997) or *Festo Corp.* v. *Shoketsu Kinzoku Kogyo Kabushiki Co.*, 535 U.S. 722 (2002), or other similar case-law or subsequent precedent should not be made if any future claims are added or amended subsequent to this Patent Application.

What is claimed is:

1. A therapeutic electro therapy device comprising:
   a transcutaneous electrical nerve stimulation (TENS) unit;
   a functional anatomical shaped electrodes in direct and continuous electrical communication with said TENS unit, said functional anatomical shaped electrodes that enables bio-movement forming a flexible winged configuration;
   a housing affixed to said electrodes and containing said TENS unit;
   wherein said TENS unit is further operationally controlled by a mobile application software that enables treatment regimes broken down into body parts or conditions; and
   wherein said TENS unit further comprises a pain tracking feature that measures a pain scale tracking before and after a treatment such as to allow a pain reduction differential to be tracked, charted and graphed, thereby allowing for user feedback to identify efficacy of treatment modalities.

2. The therapeutic electro therapy device of claim 1, wherein said electrodes further comprise a laser printed conductive silver paint as a conductive surface.

3. A therapeutic electro therapy device comprising:
   a transcutaneous electrical nerve stimulation (TENS) unit contained in a housing and attachable to a central housing attachment hub;
   an electrode having said central housing attachment hub and formed in a functional anatomical shape that enables bio-movement and further comprises:
   an outer layer formed of a thermoplastic polyurethane ("TPU") membrane or similar material having properties including elasticity, transparency, and resistance to oil, grease and abrasion;
   a first inner layer formed of polyethylene terephthalate ("PET") and forming a water or moisture barrier;
   a second inner conductive layer formed by laser printing a conductive metal based paint onto the first inner layer; and
   an adhesive inner surface provided as a final layer of an adhesive get to be peel-n-stick and self-applied and self-removed for a continuous reuse;
   wherein said electrode further comprises a range of motion hinge positioned at the central housing attachment hub of effecting both a rotational movement and an angular movement of the electrode.

4. The therapeutic electro therapy device of claim 3, wherein said electrode layers are assembled in a laminate fashion to form the pair of electrode attachment surfaces laterally extended about the central housing attachment hub that is formed to allow for the electrodes to be interconnected to the TENS unit by way of a magnetic connection.

5. The therapeutic electro therapy device of claim 3, wherein said electrode is further in a shape of a biconic, butterfly, hourglass or dogbone shaped planar member having a pair of planar, opposed wing membranes extending bilaterally from said central housing attachment hub.

6. The therapeutic electro therapy device of claim 3, wherein said outer layer is both flexible as well as capable of sustaining full color printing on the outside of the wing configuration.

7. The therapeutic electro therapy device of claim 3, further comprising a mechanism for providing a depolarization conductive current to counteract the effects of accumulated ionic impurities.

8. A transcutaneous electrical nerve stimulation (TENS) system comprising:
   a functional anatomical shaped electrode that enables bio-movement; and
   a housing containing control electronics in firm magnetic connection to the electrode, thereby allowing for full operational connectivity as well as firm mechanical positioning and retention of the housing;
   wherein said functional anatomical shaped electrode is of a wing configuration with proprietary design of shape, material composition and size;
   wherein the improvement further comprises an electrode element configuration accommodating improved motion mechanics and maneuverability while maintaining electrical contact, wherein said improvement further comprises said electrode having a soft wing construction providing a multi-planar flexibility during operation; and
   wherein said electrode further comprises a range of motion hinge positioned at a central area of a winged configuration such that both a rotational movement and an angular movement may occur.

9. The TENS system of claim 8, wherein said electrode further comprises a selected die-cut pattern forming a stepped-in wing configuration that further contributes to a lateral flexibility of the wings.

10. The TENS system of claim 8, wherein said electrode further comprises a rotational ball-joint and/or a hinge connection between a TENS device body and electrode wings such that greater motion mechanics and multi planar flexibility may be achieve.

11. The TENS system of claim 8, wherein electrode further comprises medical grade sliver paste with additives for enhancing conductivity and durability.

12. The TENS system of claim 11, further comprising multi-layered silver composite supported onto a lower exterior surface of an electrode wing membrane substrate.

13. The TENS system of claim 8, further comprising a mechanism for providing a depolarization conductive current to counteract the effects of accumulated ionic impurities.

14. The TENS system of claim 8, further comprising in combination:
   a mobile application software that enables monitoring, tracking and controlling of treatment regimes.

15. An improved transcutaneous electrical nerve stimulation (TENS) system comprising:
   an integrated and portable, disc shaped range-of-motion housing that incorporates a TENS device that is in direct and continuous electrical communication with a functional anatomical shaped electrode that enables bio-movement;
   wherein said housing further comprises an attachment mechanism that affixes directly to the electrode such that when the electrode is attached to a user the housing is supported directly thereon during use;
   wherein said electrode is configured having a soft wing construction providing a multi-planar flexibility; and
   wherein said electrode further comprises a soft wing construction incorporating a range of motion hinge at a central area such that a rotational movement may occur.

16. The improved TENS system of claim 15, further comprising conductive channeling of currents to said electrode anode and said electrode cathode.

17. A transcutaneous electrical nerve stimulation (TENS) system comprising:
   a functional anatomical shaped electrode that enables bio-movement; and
   a housing containing control electronics in firm magnetic connection to the electrode, thereby allowing for full operational connectivity as well as firm mechanical positioning and retention of the housing; and
   a mechanism for providing a depolarization conductive current to counteract the effects of accumulated ionic impurities.

* * * * *